(12) United States Patent
Dragan

(10) Patent No.: US 10,870,129 B1
(45) Date of Patent: Dec. 22, 2020

(54) VAPOR INFUSION METHOD AND DEVICE

(71) Applicant: Alexander Dragan, Brooklyn, NY (US)

(72) Inventor: Alexander Dragan, Brooklyn, NY (US)

( * ) Notice: Subject to any disclaimer, the term of this patent is extended or adjusted under 35 U.S.C. 154(b) by 527 days.

(21) Appl. No.: 15/450,928

(22) Filed: Mar. 6, 2017

Related U.S. Application Data

(60) Provisional application No. 62/303,981, filed on Mar. 4, 2016, provisional application No. 62/318,482, filed on Apr. 5, 2016.

(51) Int. Cl.
| | | |
|---|---|---|
| *B05D 1/40* | (2006.01) | |
| *A61K 31/05* | (2006.01) | |
| *A61K 31/352* | (2006.01) | |
| *A61M 11/04* | (2006.01) | |
| *A61M 15/00* | (2006.01) | |

(52) U.S. Cl.
CPC ............... *B05D 1/40* (2013.01); *A61K 31/05* (2013.01); *A61K 31/352* (2013.01); *A61M 11/04* (2013.01); *A61M 15/0066* (2014.02); *A61M 2207/00* (2013.01)

(58) Field of Classification Search
CPC ........ B05D 1/40; A61K 31/05; A61K 31/352; A61M 11/04
See application file for complete search history.

(56) References Cited

U.S. PATENT DOCUMENTS

| | | | |
|---|---|---|---|
| 7,114,503 B2 | 10/2006 | Vialle | |
| 8,602,036 B2 | 12/2013 | Marquez et al. | |
| 8,739,802 B2 | 6/2014 | Fagg | |
| 8,851,084 B2 | 10/2014 | Lemmouchi et al. | |
| 9,078,471 B2 | 7/2015 | Sampson et al. | |
| 9,642,394 B2 | 5/2017 | Branton et al. | |
| 9,661,875 B2 | 5/2017 | Karles et al. | |
| 9,675,105 B2 | 6/2017 | Sakai | |
| 2013/0032159 A1* | 2/2013 | Capuano ................ A24F 1/30 131/329 |
| 2014/0230832 A1* | 8/2014 | Saliman ................. A24F 1/30 131/173 |
| 2015/0013699 A1* | 1/2015 | Ellis .................... A24F 47/008 131/329 |
| 2016/0037825 A1* | 2/2016 | Stein ..................... A24F 1/30 131/328 |
| 2016/0235117 A1* | 8/2016 | Mehio ................... A24F 1/30 |

* cited by examiner

*Primary Examiner* — Erik Kashnikow
*Assistant Examiner* — Preston Smith
(74) *Attorney, Agent, or Firm* — Sheridan Ross P.C.

(57) ABSTRACT

A method and device are provided that forms a vapor, aerosol, or suspension of a substance or component thereof, the substance or component thereof being a herbal material; passes the vapor, aerosol, or suspension through an edible sorbent; and collects the substance or component thereof on the edible sorbent to provide a food product.

20 Claims, 8 Drawing Sheets

VAPOR INFUSION METHOD AND DEVICE

CROSS REFERENCE TO RELATED APPLICATION

The present application claims the benefits of U.S. Provisional Application Ser. No. 62/303,981, filed Mar. 4, 2016, and 62/318,482, filed Apr. 5, 2016, both entitled "VAPOR INFUSION DEVICE", each of which is incorporated herein by this reference in its entirety.

FIELD

The disclosure relates generally to food products and particularly to food products derived from herbal substances.

BACKGROUND

For many centuries, humans have consumed various herbal substances (including, but not limited to, tobacco, *cannabis, salvia*, DMT, and various opioids) through the mechanism of inhalation for both recreational and medicinal purposes. As new technologies developed, the methods of consumption for these substances became varied. During the late 20th and early 21st centuries many mechanical devices were developed to assist with this form of consumption, most notably the vaporizer. These devices typically require the user to insert a small amount of substance into a receptacle, which is then heated to a particular temperature, thus releasing the various compounds in the form of a vapor which is then inhaled by the user. Although this is typically perceived as a more convenient form of consumption than other methods, it is not without drawbacks. Many individuals that suffer from lung diseases and other ailments utilize inhaled herbal supplements for relieving various symptoms (such as chronic pain). These individuals are often unable to utilize a vaporizer (or any device that requires inhalation) due to their conditions and thus, are forced to either forgo needed treatment or resort to other time consuming and costly methods of consumption, such as baking (which they may be unable to perform due to physical difficulties). Moreover, many individuals able to consume herbal substances through regular vaporization lack a solution that allows them to utilize vaporization to its fullest potential (chiefly those with medical issues that require regular dosage).

There is a need to create a hybrid solution for those engaged in recreational and/or medicinal use of herbal substances by providing a means for each individual to choose which method they prefer based on their unique circumstances.

There is a need to provide individuals engaging in recreational and/or medicinal use of herbal substances (particularly *cannabis*) with a solution that allows the user to experience a longer lasting effect of the substance without the need to re-up their dosage. Although many devices are available for assisting in the consumption of various herbal substances there is no current method of consumption (other than baking or creating oils, which can be both time consuming and costly) that allows users to create a portable and easily concealable substance that contains the activated substance, which can be carried on a person and taken orally.

SUMMARY

These and other needs are addressed by the various aspects, embodiments, and configurations of the present disclosure. The following is intended to be a brief summary of the disclosure and is not intended to limit the scope of the disclosure.

A method can include the steps:
forming a vapor, aerosol, or suspension of a substance or component thereof, the substance or component thereof being a herbal material;
passing the vapor, aerosol, or suspension through an edible sorbent; and
collecting the substance or component thereof on the edible sorbent to provide a food product.

A device can include:
an input for a vapor, aerosol, or suspension of a substance or component thereof, the substance or component thereof being a herbal material;
a substrate comprising one or more fluid pathways;
the edible sorbent positioned in the one or more fluid pathways to contact the vapor, aerosol, or suspension passing through the one or more fluid pathways to collect the substance or component thereof on the edible sorbent to provide a food product; and
an output for the vapor, aerosol, or suspension discharged from the one or more fluid pathways.

The vapor, aerosol, or suspension can be a vapor.

The substance can be one or more of *cannabis* and tobacco, and the component thereof can be one or more of nicotine, tetrahydrocannabinol, cannabinol, cannabigerol, tetrahydrocannabivarin, cannabidivarin, and cannabichromene.

The substance can be one or more of *cannabis* and tobacco, and the component thereof can be one or more of nicotine and a cannabinoid.

The device can include a heat source, the heat source being positioned near the input to heat the substance.

The substance can be supported on a screen positioned between the heat source and the support, and the output can be positioned on an opposing side of the support from the input.

The vapor, aerosol, or suspension can be an aerosol or suspension.

The input can include one or more nozzles to provide a liquid stream comprising the substance or component thereof.

The one or more nozzles can be at an end of one or more needles.

The edible sorbent can be at least partially enclosed in a container. The container can be supported in the one or more fluid pathways, and the one or more needles can be in fluid communication with the interior of the container.

The substance can be in a sorbent receptacle in fluid communication with the one or more needles, the one or more fluid pathways, and the outlet.

The device can include a plunger, wherein the aerosol or suspension is formed when a user displaces the plunger towards the nozzles.

The plunger can have a hollow interior formed by a body member of the plunger and a lid member engaging the body member.

The output comprises a mouthpiece for a user that enables the user to ingest the discharged vapor, aerosol, or suspension.

The present disclosure can provide a number of advantages depending on the particular configuration. The collection and injection devices of this disclosure can provide an effective hybrid solution for those engaged in recreational and/or medicinal use of herbal substances and a means for each individual to choose which method they prefer based on their unique circumstances. The devices can provide individuals engaging in recreational and/or medicinal use of herbal substances (particularly *cannabis*) with a solution that allows the user to experience a longer lasting effect of the substance without the need to re-up their dosage. It can provide a method of consumption that allows users to create a portable and easily concealable substance that contains the activated substance, which can be carried on a person and taken orally.

These and other advantages will be apparent from the disclosure of the aspects, embodiments, and configurations contained herein.

As used herein, "absorbent" is a material that incorporates a substance in one state and converts it into another of a different state (e.g. liquids being absorbed by a solid or gases being absorbed by a liquid). Absorption is a physical or chemical phenomenon or a process in which atoms, molecules, or ions enter some bulk phase—gas, liquid or solid material. This is a different process from adsorption, since molecules undergoing absorption are taken up by the volume, not by the surface (as in the case for adsorption).

As used herein, "adsorbent" is a material in which atoms, ions, biomolecules, or molecules of gas, liquid, or dissolved solids adhere to a surface. This process creates a film of the adsorbate (the molecules or atoms being accumulated) on the surface of the adsorbent. It differs from absorption, in which a fluid permeates or is dissolved by a liquid or solid. Similar to surface tension, adsorption is generally a consequence of surface energy. The exact nature of the bonding depends on the details of the species involved, but the adsorption process is generally classified as physisorption (characteristic of weak van der Waals forces)) or chemisorption (characteristic of covalent bonding). It may also occur due to electrostatic attraction.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C", "A, B, and/or C", and "A, B, or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "herbal material" refers to any plant or portion thereof, including herbs, spices, or substance in or derived therefrom used for food, flavoring, medicine, or fragrances for their savory or aromatic properties. Some plants contain phytochemicals that have effects on the body. Some plants have psychoactive effects on the body.

The term "means" as used herein shall be given its broadest possible interpretation in accordance with 35 U.S.C., Section 112(f) and/or Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the disclosure, brief description of the drawings, detailed description, abstract, and claims themselves.

As used herein, a "nozzle, is a cylindrical or round spout at the end of a pipe, hose, or tube, used to control a jet of gas or liquid.

As used herein, "sorbent" is a material that sorbs another substance; that is, the material has the capacity or tendency to take it up by sorption.

As used herein, "sorb" and cognates thereof mean to take up a liquid or a gas by sorption. As used herein, "sorption" and cognates thereof refer to adsorption and absorption, while desorption is the reverse of adsorption.

Unless otherwise noted, all component or composition levels are in reference to the active portion of that component or composition and are exclusive of impurities, for example, residual solvents or by-products, which may be present in commercially available sources of such components or compositions.

All percentages and ratios are calculated by total composition weight, unless indicated otherwise.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein. By way of example, the phrase from about 2 to about 4 includes the whole number and/or integer ranges from about 2 to about 3, from about 3 to about 4 and each possible range based on real (e.g., irrational and/or rational) numbers, such as from about 2.1 to about 4.9, from about 2.1 to about 3.4, and so on.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below. Also, while the disclosure is presented in terms of exemplary embodiments, it should be appreciated that individual aspects of the disclosure can be separately claimed.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
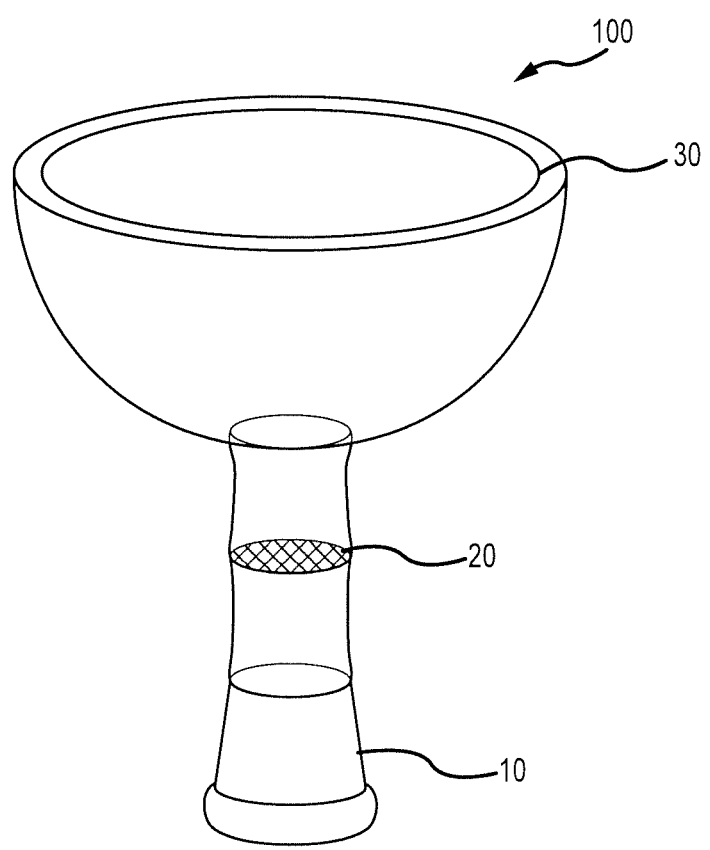
FIG. 1 is an isometric view of a lower section of a collection device according to an embodiment.
Figure 2A:
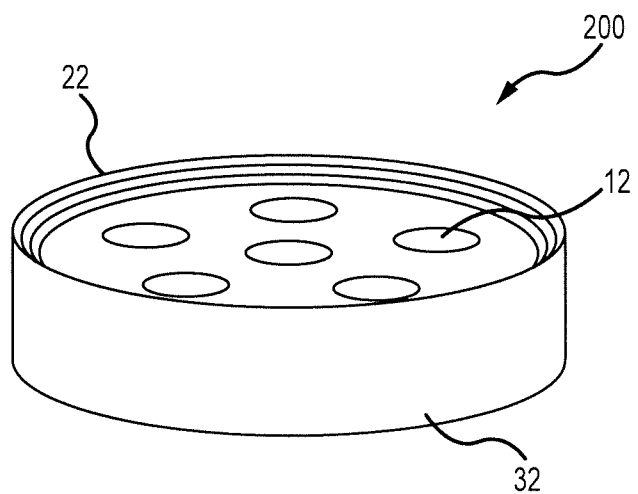
FIGS. 2A-B are isometric and plan views of a middle section of the collection device according to an embodiment.
Figure 2B:
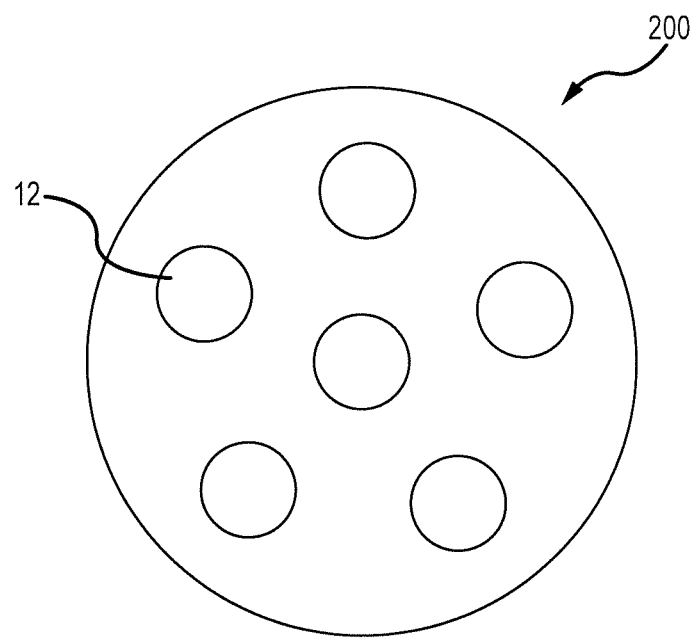

The collection and injection devices of this disclosure can capture the vapor after being released from the solid herbal substance with another solid or semi-solid material that is either permeable (as to allow the vapor to pass through and be consumed normally by a user while it is simultaneously being absorbed) or not permeable (so that it captures the full extent of any vapor that attempts to pass through it), with the intent of consuming the sorbent material (containing the captured vapor) afterwards. Through this method, it is possible to collect the condensed vapor and concentrate it into a form which can later be consumed orally.

The collection and injection devices of this disclosure can individually or collectively (depending on the substance) extract, from the substance, one or more compounds or components of interest. By way of example and not limitation, substances include herbal materials, such as *cannabis*, tobacco, edible oils, and combinations thereof (e.g., *cannabis* and coconut oil) and the target one or more compounds include nicotine and cannabinoids (e.g., tetrahydrocannabinol, cannabinol, cannabigerol, tetrahydrocannabivarin, cannabidivarin, and cannabichromene) via vaporization (either conduction or convection methods) or atomization (in a similar method that modern vaporizers use) by including the intermediate step of adding an sorbent material between the raw herb and the mouthpiece (or at any point after the material has been transformed into vapor). This list is not exhaustive; the components of interest and host substances can be any number of other materials depending on the application.

The solid or semi-solid sorbent materials may be proprietary compounds that allow for optimal absorption of the herbal substance, or simple compounds such as cellulose, or silica, in a porous form, specifically constructed for the purposes of this device or in a natural form (ex. cotton). As stated above, this material will likely be constructed out of any material, whether organic, inorganic, or a combination thereof. It is typically an organic and non-hazardous material that can be easily consumed by humans (such as cellulose, protein-based polymers, hydrocolloid polymers, polypeptide polymers, lipid polymers, or other edible polymers and composites thereof in the form of a permeable and porous matrix) or an inorganic and non-hazardous material (such as silica or silica gel). Its construction can take a variety of forms which will likely be either porous or semi-porous and permeable or semi-permeable so as to allow for optimal vapor absorption and passage (such as a layered lattice structure).

The device can have a method of taking the sorbent material (after it has absorbed the appropriate amount of vapor) and packaging it through some mechanical means, into an object that can be more easily consumed (such as placing it inside one or multiple capsules). Alternatively, there could be a structure (in the same or similar location) that houses several small capsules or tablets which are prepared with sorbent material.

These capsules, or tablets, contain the sorbent material within them and allow for the vapor to pass through these structures, the intent of which is that a user can easily remove and consume them once the absorption is finished, rather than relocating the sorbent material into similar structures through a mechanical process afterwards. This variation allows for a less mechanically complex device.

While the sorbent material is discussed with reference to sorbent materials, it is to be understood that any adsorbent material or any other sorbent can be used alternatively or in addition to the sorbent material.

This collection and injection devices of this disclosure can be used with a broad variety of other adsorbents and is not limited to those above. Once the sorbent is sufficiently saturated with the herbal substance (which is not limited to any specified level of saturation and can, in-fact, potentially be measured by a device, such as a laser, and adjusted by the user to their desired amount) the secondary part of the device (which is either directly integrated into the first or exists as a separate entity operated by the user) can inject a solvent (typically in the form of an oil, including but not limited to, coconut oil, olive oil, canola oil, etc) and finally dispense the saturated substance (which would already be in a consumable form), for the user to consume either immediately, or at a later time.

The collection device or injection device of this disclosure can serve as an adapter to or as a component of a vaporizer device, or as a combination of the two (with the collection device as integrated and the injection device as separate from the vaporizer unit). The collection and injection devices of this disclosure can alleviate many of the concerns issued with the consumption of herbal substances in smoke or vapor form for those medically unable to receive them in such a manner and also with the dual concern of portability and methods of discrete concealment.

The collection or injection devices of this disclosure can provide a mechanism for users with the desire and/or need for regular dosage with a manner to experience sustained effects of the herbal substance (longer than with any other method that exists at this present time) while simultaneously allowing them to conserve more of their raw herbal material.

The collection or injection devices of this disclosure can dispense a solid or semi-solid (whether through gel-like means or encapsulation of a liquid) substance containing the various compounds located in the vapor so that the user can easily conceal, as one would with any pill-like structure, and transport on their person.

This collection or injection devices of this disclosure can be implemented or configured in any number of ways and the implementation and configuration described herein is presented for illustration purposes only.

An embodiment of a collection device 400 is shown in FIGS. 1, 2A-B, 3 and 4.

With reference to FIG. 1, a lower section 100 of a collection device 400 (FIG. 4) is depicted. A lower port 10 of the lower section 100 is configured to fit directly over, and be received by, a heating element (not shown) of the collection device 400 (as either part of a separate entity and/or integrated with the collection device 400) so it is typically made of a heat resistant material that can withstand the maximum temperatures that the heating element produces without altering the form of (or deforming) or otherwise causing damage to the lower section 100. Glass is commonly the material of choice for the construction of the lower section 100, but other heat resistant materials can be used. The lower section 100 can also house the herbal/food substance to be heated.

The lower port 10 can contact the heating element. The lower port 10 is positioned close enough to the heating element so as to allow for a selected herbal/food substance, supported by a mesh 20, to be vaporized efficiently.

The mesh 20 is commonly a removable and permeable screen (likely constructed of metal and being relatively thin) that the herbal/food substance will sit upon. An indentation in the inside of the material can be employed to create a seat for the mesh 20 to sit upon. This mesh 20 should ideally be removable and replicable (or replaceable) if it gets sufficiently dirty.

A top 30 of the lower section 100 can have a threaded surface, or screw grooves, to match those at the bottom of the middle section (FIG. 2) or some other manner to fasten itself to this section as to form an airtight seal.

Figure 4:
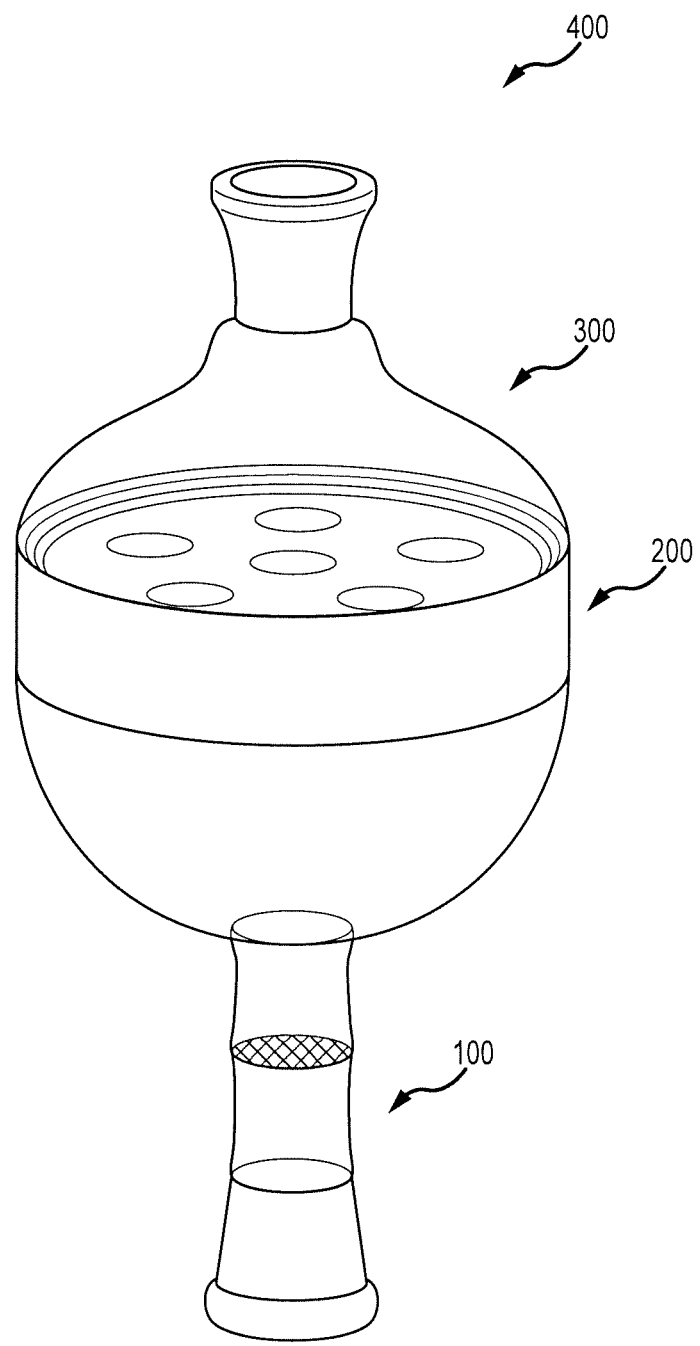
FIG. 4 is an isometric view of the assembled collection device ready for use according to an embodiment.
Figure 5:
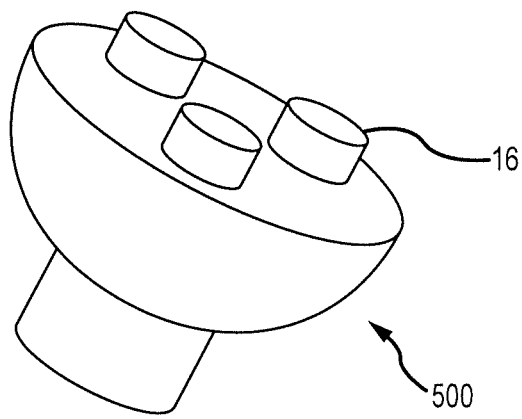
FIG. 5 is an isometric view of a lower section of an injection device according to an embodiment.
Figure 6:
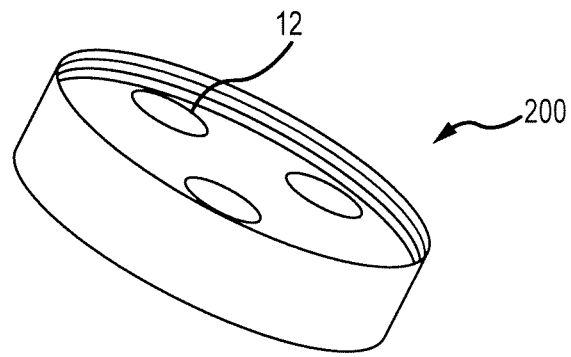
FIG. 6 is an isometric view of a middle section of an injection device according to an embodiment.
Figure 7A:
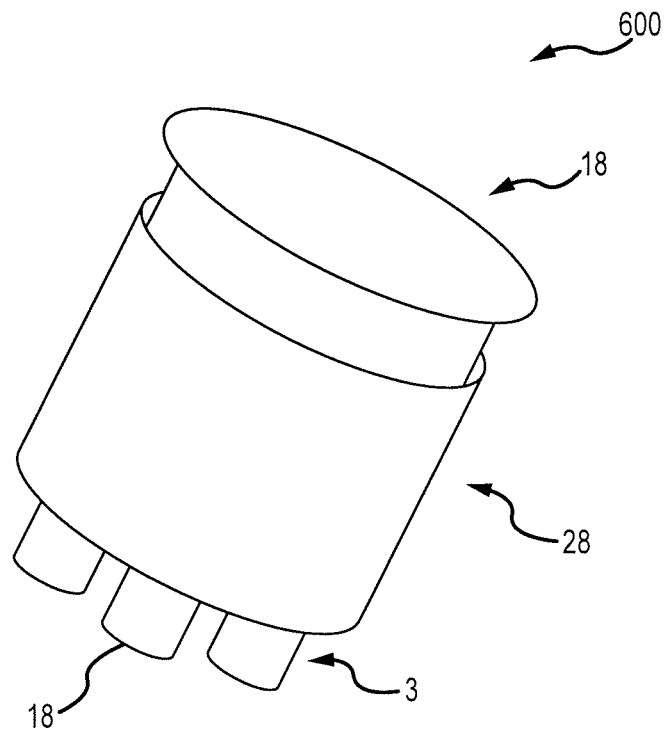
FIGS. 7A-B are various isometric views of an upper section of the injection device according to an embodiment.
Figure 7B:
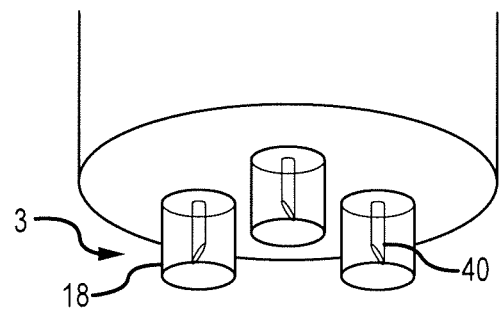
Figure 8A:
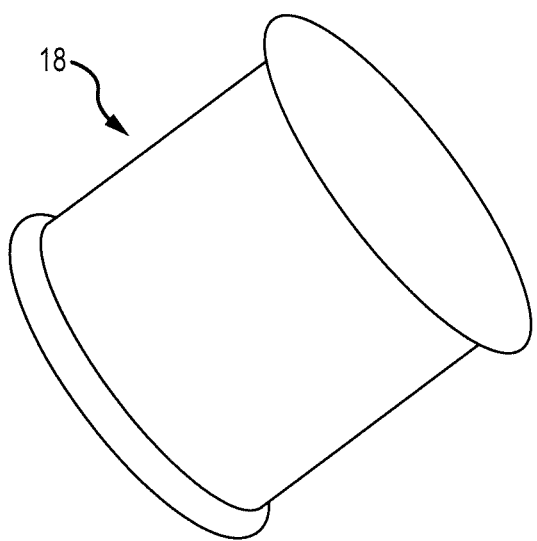
FIGS. 8A-B are dissembled views of the upper section.
Figure 8B:
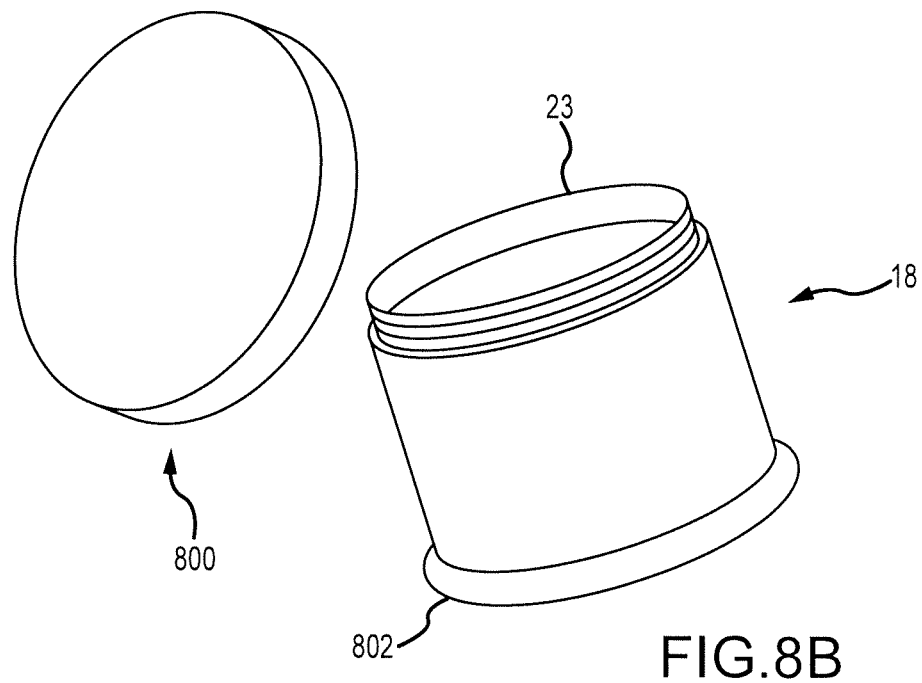

FIG. 2 depicts the middle section 200 of the collection device 400 (as either part of a separate entity and/or integrated with a collection device) and houses an sorbent material. The middle section 200 is configured to fit directly on top of, and to be received by, the lower section 100 of FIG. 1 forming an air tight or hermetic seal therebetween. While FIG. 4 shows one middle section 200, it is to be appreciated that multiple middle sections can be stacked one on top of the other between the upper and lower sections. The through holes (of which there can be one or many) receive and contain the sorbent material (which can be inserted and removed by a user) and allows the vapor to pass from the lower section through to the upper section. The material that comprises this part of the device is generally also be heat resistant.

The openings, or through holes, 12 pass through the entirety of the middle section 200 from top to bottom. These holes 12 hold the sorbent material in whatever form it is in and thus can take any form or shape needed to accomplish the task. There may be one or many openings depending on what allows optimal absorption.

The top 22 of the middle section 200 can have threads or screw-grooves or some other method to attach (or sit on top of, forming an airtight seal with, the) middle section 200 to other stacked middle sections 200 (in the case of stacking multiple middle sections) and to the upper section 300 of the device 400 as necessary.

The bottom 32 of the middle section 200 can also have threads or screw-grooves or some other method of attaching the middle section to (or allowing it to fit and form an airtight seal with) the lower section 100 as necessary. The bottom 32 may need to be slightly smaller than the top 22 to allow for multiple middle section units to be stacked. Any other solution for stacking the middle sections that also allows them to connect to both the lid and bottom sections can be employed.

Figure 3:
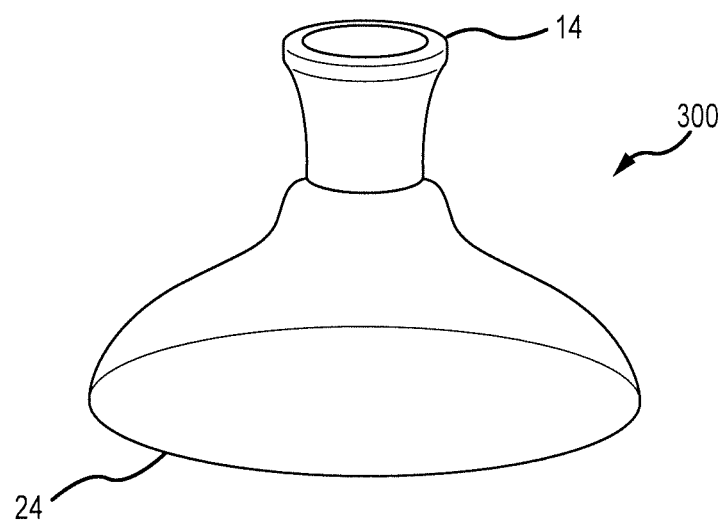
FIG. 3 is an isometric view of an upper section of the collection device according to an embodiment.

FIG. 3 depicts the upper section 300 of the collection device 400 (as either part of a separate entity and/or integrated with the collection device). The upper section 300 is configured to fit directly on top of, and to be received by, the middle section 200 forming an air tight or hermetic seal therebetween. The upper section 300 has an opening at the top that can be connected to a bag or other inhalation device (such as a whip or other connector) allowing the vapor to pass through for oral consumption by one or multiple users.

The top 14 of the upper section 300 can fit securely to a bag (which allows it to be filled with vapor) or a mouthpiece (such as a "whip" or other device) that allows one or multiple users to inhale the vapor which has been channeled through the collection device 400 and the sorbent material.

The bottom 24 of the upper section 300 can be threaded or have screw-grooves or some other method to attach itself to the middle section 200 of the collection device 400 and form an air-tight seal.

FIG. 4 depicts the fully assembled collection device 400 with the lower, middle, and upper sections stacked one-on-top-of-the-other. In this configuration, the collection device 400 is ready for use (without the sorbent or material to be vaporized pictured). The fully assembled collection device 400 should be airtight from the bottom opening to the top as to allow the vapor to be channeled through properly.

In some embodiments of this disclosure, there will be a method of reconnecting the top opening, via a tube (or a similar structure), back into the collection device, thus creating a closed (or semi-closed) circulation within that is able to capture more vapor in either the primary sorbent, and/or a secondary sorbent, with the purpose of collecting additional vapor if the user decides to not use the device for inhalation during a specific session. This modification can allow the user more flexibility in using the device and is important for those with medical issues that prevent them from using a device for inhalation; in this manner, a user with such a medical condition will be able to use the device solely to construct edible materials that are saturated with the vapor.

Depending on the substance to be collected, the collection device can collect a selected substance by means of distillation, in which a component of material, typically in the form of a liquid, is separated from the material by evaporation or vaporization and condensation of the vaporized component on a selected surface, such as a sorbent material. The distillation is generally not used as a true purification method but more to transfer volatiles from the source substance to the distillate. A solvent can be added to effect extractive distillation in which distillation is performed in the presence of a miscible, high boiling, relatively non-volatile component, the solvent, that forms no azeotrope with the other components in the mixture. Other types of distillation can be employed, such as azeotropic distillation in which components of the substance interact to create properties unique to the substance.

Depending on the substance to be collected, the collection device can collect a selected substance by means of sublimation, in which a component of material, typically in the form of a solid, transitions directly from the solid to the gas phase without passing through the intermediate liquid phase. Sublimation is an endothermic phase transition that occurs at temperatures and pressures below a substance's triple point in its phase diagram. The reverse process of sublimation is deposition or desublimation, in which a substance passes directly from a gas to a solid phase. Once in the vapor phase, the component can be separated from the material by condensation or desublimation of the vaporized component on a selected surface, such as a sorbent material.

This device in its entirety (or any combination of its elements) is either intended to be either a separate entity or integrated into a vaporization device.

An embodiment of an injection device is shown in FIGS. 5-9. The injection device can form an aerosol of the substance or a target component in the substance. An aerosol is a colloid of fine solid particles or liquid droplets, in air or another gas. The liquid or solid particles have diameter mostly smaller than about 1 μm or so. The injection device can form a suspension of the substance or the target component. A suspension is a mixture of fine solid particles or liquid droplets, most having a diameter greater than 1 μm or so in air or another gas. A solvent may be used to solubilize the substance or a component thereof in a liquid phase for aerosol or suspension formation.

FIG. 5 represents a bottom section 500 of an injection device (as either a separate entity and/or as part of a unit integrated with a vaporization device) and, when used, houses the bottom half of the casing(s) 16 (made of an edible material including, but not limited to, gelatin, silica, cellulose, etc) that encapsulate(s) the sorbent and the substance (once injected). The number of holding units 16 (a unit representing a single hollow protrusion intended to hold a single half of a casing) will correspond directly to, and line up with, the number of holes 12 in FIG. 6 of the injection device.

The through holes 12 of middle section 200 of FIG. 6 align with corresponding units 16 in the lower section 500. As noted, the number of through holes and units 16 can vary based on the optimization of each device. The holding units 16 will house half of the casing/capsule, holding it in place as it is inserted into the middle section 200. Each holding unit 16 is hollow, allowing the casing/capsule half to sit inside comfortably and providing it with enough support so it can be inserted into the middle section 200 (and ultimately connect flawlessly with its top half housed in holding unit 18 with ease.

The middle section 200 can have any number of through holes (which number is consistent with how many holding units 16 and 18 are on the injection device).

FIGS. 7A-B depict an upper section 600 of the injection device (as either a separate entity and/or as part of a unit integrated with a vaporization device) which includes first and second members, the first member 18 being received by and fitting telescopically and movably into the second member 28. The holding units 18 underneath (a unit representing a single hollow protrusion, along with the injector needle 40 (having a nozzle at an end thereof), intended to hold a single half of a casing) the receptacle half of the second member 28 is intended to house the casing(s) that encapsulate(s) the sorbent and the substance (once injected). The number of holding units directly corresponds to, and lines up with, both the number of holding units in FIG. 5 and the number of through holes 12 in FIG. 6. FIG. 2B represents a viewing angle from the bottom of the second member 28 with transparent holding units to view injector needles that protrude from the bottom of the injection device 700.

The first member 18 represents the "plunger"/"solvent receptacle" when it is inserted into the top piece of the injection device 700.

The second member 28 represents the receptacle half of the upper section 600 and has a body member 802 and lid member 800 (that can be attached by any mechanism such as threaded engagement (as shown), frictional engagement, and the like). Before the plunger is inserted, the substance is poured into the interior of the second member 28, which acts as a receptacle (which is hollow, thus allowing the "plunger"/"solvent receptacle" along with the substance to fit inside) which, when the plunger is pressed down, will force the substance through the injector needles 40, and into the sealed casing/capsule 18 and 16. It is important to note that the injector needles may be part of a removable insert (since the needles are likely to suffer wear and tear over time) that fits inside and lines the bottom of the second member 18.

The middle section 200 will hold in place the upper and lower halves 16 and 18 of each of the holding units. The upper and lower halves of each holding unit fit together, typically telescopically with one of the upper and lower halves receiving the other of the upper and lower halves, to form a fully enclosed hollow interior. The casing/capsule half can sit inside the hollow interior comfortably (allowing the needle to penetrate the casing/capsule). The upper half 18 of each holding unit can be inserted into the middle section 200 (and ultimately connect flawlessly with its bottom half 16 housed in the lower section 500 with ease.

The needles 40 will penetrate the casing (and likely serve the dual purpose of holding it in place) and allow the substance to enter from the second member 28 as the first member 18 is pressed down by the user. These needles (which could be attached to a removable insert) can be made of varying materials of different shapes and sizes and may not even take the shape of needles if the casing/capsule ultimately takes on another form.

FIG. 8 depicts the first member 18, which acts as a "plunger"/"solvent receptacle" part of the injection device 700 (as either a separate entity and/or as part of a unit integrated with a vaporization device). The first member 18 sits movably inside of the second member 28. FIG. 2A shows what the first member 18 looks like when it is separate from the second member 28, the bottom of which is attached to the lid member 800 composed of either a rubber or other material (or potentially crafted entirely of that material) that allows the part to form an airtight (or near airtight) seal when placed inside of the second member 28. This allows the first member 18 to be used as a plunger which will push the liquid substance (which is poured into the interior of the second member 28 which acts as a receptacle) through the injector needles 40 and into the interior of the injection device 600 (once fully closed over the sorbent material), allowing it to saturate the sorbent material while inside the lower section 500. FIG. 8B represents the unit with the (rubber or other material) lined (or crafted entirely of that material) cap removed, revealing that the first member 18 is hollow. The hollow nature of the "plunger" is meant to serve as a "substance receptacle" if the substance requires preheating to achieve a liquid state (some substances, chiefly coconut oil, tend to be solid at room temperature). The first member 18 should be constructed of a material that is microwave safe. This feature of the device may or may not be necessary depending on the nature of the substance used and/or if the unit is integrated into a vaporizer device.

The first member 18 acts as the "plunger"/"solvent receptacle" piece as seen in its assembled and disassembled (with the lid member 800 removed) forms of FIGS. 8A and 8B. The first member 18 may or may not exist in its current form depending on a number of factors (e.g., whether the device exists as part of an internal unit housed within a vaporizer device). However some form of vaporization assistance is normally required for the substance to make its way from the receptacle (FIGS. 7A and 7B) into the casing/capsule (or whatever form the sorbent is housed within or part of). Depending on the nature of the substance, it may or may not be necessary for the first and second members to form a hollow cavity and serve as a receptacle that allows for the substance in solid form (such as coconut oil) to be heated by a device (such as a microwave); however, if the device is used for this purpose, it will likely need to be constructed of a microwave safe and/or heat resistant material.

The removable lid member 800 (assuming the piece is hollow) is either constructed out of a, or lined with, an impermeable material (such as rubber) that is semi-flexible and able to serve as the bottom portion of the plunger which will ultimately form an airtight (or near airtight) seal, allowing the first member 18 to force the substance through the injector needles 40 and into the casing/capsule (assuming that it is part of the device).

The open end 23 of the body member 802 comprises an attachment point for the lid member 800 (if one exists). The receptacle (if necessary) will be hollow to allow for substances, which may be solid at room temperature (ex: coconut oil), to be heated within. Assuming that this device does not constitute part of the internal structure of a specialized vaporizer, the hollow receptacle can allow users to utilize the device for all functions involved in the process of creating vapor-infused solids. One could theoretically heat up a solid solvent in another receptacle, such as a small pot.

Figure 9:
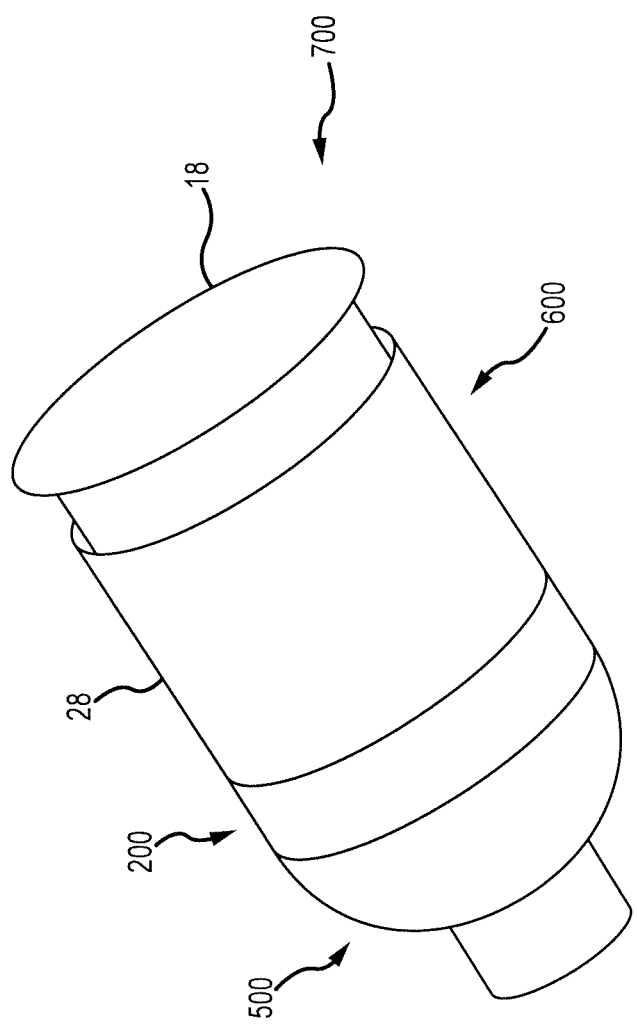
FIG. 9 is an isometric view of the assembled injection device ready for use according to an embodiment.

FIG. 9 shows the upper, middle and lower sections fully assembled to form the injection device 700. The fully assembled injection device 700 seals the (now complete) casing/capsule over the sorbent material in the lower section 500 (which would now contain the active compounds absorbed from the vapor). Once the sorbent is sealed within, the substance would be poured into the second member 28 of FIG. 7 and the first member 18 would be pressed down inside the second member 28, pushing the substance through the needles 18 (which pierce through the casing/capsule 16) into the casing/capsule, and saturating the sorbent. Once the sorbent is fully saturated with the substance, the first and second members can be carefully removed, leaving the casing/capsule(s) intact with the substance-saturated sorbent, ready for consumption.

FIG. 9 depicts the fully assembled injection device 700 before and during the injection process. This depiction may represent a device separate from the collection device (with the exception of FIG. 6) or a possible configuration for an internal structure (containing some or all of the components of the vaporization device) of a vaporizer unit, which may or may not include internal structures represented in the injection device drawings.

A number of variations and modifications of the disclosure can be used. It would be possible to provide for some features of the disclosure without providing others.

In one embodiment, the collection device can use steam distillation, in which steam is introduced into the lower port. Steam distillation can distill compounds which are heat-sensitive. The temperature of the steam is easier to control than the surface of a heating element, and allows a high rate of heat transfer without heating at a very high temperature. This process involves bubbling steam through a heated mixture of the raw material. By Raoult's law, some of the target compound will vaporize (in accordance with its partial pressure). The vapor mixture is cooled and condensed, usually yielding a layer of oil and a layer of water.

In one embodiment, the collection device can use vacuum distillation in which distillation is performed under a vacuum. Some compounds have very high boiling points. To boil such compounds, it is often better to lower the pressure at which such compounds are boiled instead of increasing the temperature. Once the pressure is lowered to the vapor pressure of the compound (at the given temperature), boiling and the rest of the distillation process can commence.

The present disclosure, in various aspects, embodiments, and configurations, includes components, methods, processes, systems and/or apparatus substantially as depicted and described herein, including various aspects, embodiments, configurations, subcombinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, e.g., for improving performance, achieving ease and\or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An assembly, comprising:

a mesh supporting a herbal substance comprising a substance or component to be ingested that, when heated, forms a vapor, aerosol, or suspension comprising the substance or component to be ingested;

a substrate, positioned downstream at a distance from the mesh, comprising one or more fluid pathways for the vapor, aerosol, or suspension, wherein the vapor, aerosol, or suspension flows through the substrate in a first direction;

an edible sorbent positioned in the one or more fluid pathways to contact the vapor, aerosol, or suspension passing through the one or more fluid pathways to collect a portion of the substance or component to be ingested on the edible sorbent, the edible sorbent being permeable or semi-permeable to pass the vapor, aerosol, or suspension;

an output for the vapor, aerosol, or suspension discharged from the one or more fluid pathways after contact with the edible sorbent, the output being in communication with a bag or inhalation device enabling inhalation of the vapor, aerosol, or suspension by a user;

one or more nozzles in fluid communication with the one or more fluid pathways; and a plunger in fluid communication with the one or more nozzles, configured to force a liquid solvent through the one or more nozzles while the edible solvent is positioned in the one or more fluid pathways to inject the solvent along the one or more fluid pathways in a second direction to contact the edible sorbent comprising the collected portion of the substance or component to be ingested and provide a food product, wherein the first and second directions are transverse to each other.

2. The assembly of claim 1, wherein the vapor, aerosol, or suspension is a vapor, wherein the herbal substance is one or more of *cannabis* and tobacco, wherein the substance or component to be ingested is one or more of nicotine, tetrahydrocannabinol, cannabinol, cannabigerol, tetrahydrocannabivarin, cannabidivarin, and cannabichromene and further comprising a heat source, the heat source being positioned near the near the mesh to heat the herbal substance.

3. The assembly of claim 2, wherein the mesh is a screen positioned between the heat source and the substrate, wherein the output is positioned on an opposing side of the screen from the heat source, wherein the sorbent comprises an organic and non-hazardous material selected from the group consisting essentially of cellulose, protein-based polymers, hydrocolloid polymers, polypeptide polymers, lipid polymers, or other edible polymers and composites thereof in the form of a permeable and porous matrix or an inorganic and non-hazardous material selected from the group consisting essentially of silica, silica gel, and mixtures thereof, and wherein the output comprises a mouthpiece for a user that enables the user to ingest the discharged vapor, aerosol, or suspension.

4. The assembly of claim 1, wherein the vapor, aerosol, or suspension is an aerosol or suspension, wherein the herbal substance is one or more of *cannabis* and tobacco, and wherein the substance or component to be ingested is one or more of nicotine and a cannabinoid.

5. The assembly of claim 4, wherein the one or more nozzles are at an end of one or more needles, wherein the edible sorbent is at least partially enclosed in a container, the container being supported in the one or more fluid pathways, and wherein the one or more needles are in fluid communication with the interior of the container.

6. The assembly of claim 5, wherein the edible sorbent is in a sorbent receptacle in fluid communication with the one or more needles, the one or more fluid pathways, and the output.

7. The assembly of claim 6, wherein the liquid solvent is one or more of coconut oil, olive oil, and canola oil and further comprising a receptacle for the solvent.

8. The assembly of claim 1, wherein the plunger comprises a hollow interior formed by a body member of the plunger and a lid member engaging the body member.

9. A system, comprising:

a mesh supporting a herbal substance comprising a substance or component to be ingested that, when heated, forms a vapor, aerosol, or suspension comprising the substance or component to be ingested, the herbal substance being one or more of tobacco and *cannabis;* a substrate, positioned downstream of the mesh, comprising one or more fluid pathways for the vapor, aerosol, or suspension, wherein the vapor, aerosol, or suspension flows through the substrate in a first direction;

an edible sorbent positioned in the one or more fluid pathways to contact the vapor, aerosol, or suspension passing through the one or more fluid pathways to collect a portion of the substance or component to be ingested on the edible sorbent, the substance or component being one or more of nicotine and a cannabinoid and the edible sorbent being permeable or semi-permeable to pass the vapor, aerosol, or suspension;

an output for the vapor, aerosol, or suspension discharged from the one or more fluid pathways after contact with the edible sorbent, the output being in communication with a bag or inhalation device enabling inhalation of the vapor, aerosol, or suspension by a user;

one or more nozzles in fluid communication with the one or more fluid pathways; and a plunger, in fluid communication with the one or more nozzles, configured to force a liquid solvent through the one or more nozzles while the edible solvent is positioned in the one or more fluid pathways to inject the solvent along the one or more fluid pathways to contact the edible sorbent comprising the collected portion of the substance or component to be ingested to provide a food product, wherein the first and second directions are transverse to each other.

10. The system of claim 9, wherein the vapor, aerosol, or suspension is a vapor, wherein the component is one or more of nicotine, tetrahydrocannabinol, cannabinol, cannabigerol, tetrahydrocannabivarin, cannabidivarin, and cannabichromene, wherein the substance or component to be ingested is one or more of nicotine, tetrahydrocannabinol, cannabinol, cannabigerol, tetrahydrocannabivarin, cannabidivarin, and cannabichromene, wherein the sorbent comprises an organic and non-hazardous material selected from the group consisting essentially of cellulose, protein-based polymers, hydrocolloid polymers, polypeptide polymers, lipid polymers, or other edible polymers and composites thereof in the form of a permeable and porous matrix or an inorganic and non-hazardous material selected from the group consisting essentially of silica, silica gel, and mixtures thereof, and further comprising a heat source, the heat source being positioned near the input to heat the herbal substance.

11. The system of claim 10, wherein mesh comprises a screen positioned between a heat source and the output, wherein the substance or component to be ingested is one or more of nicotine, tetrahydrocannabinol, cannabinol, cannabigerol, tetrahydrocannabivarin, cannabidivarin, and cannabichromene, wherein the sorbent comprises an organic and non-hazardous material selected from the group consisting essentially of cellulose, protein-based polymers, hydrocolloid polymers, polypeptide polymers, lipid polymers, or other edible polymers and composites thereof in the form of a permeable and porous matrix or an inorganic and non-hazardous material selected from the group consisting essentially of silica, silica gel, and mixtures thereof, and wherein the output comprises a mouthpiece for a user that enables the user to ingest the discharged vapor, aerosol, or suspension.

12. The system of claim 9, wherein the substance or component to be ingested is one or more of nicotine, tetrahydrocannabinol, cannabinol, cannabigerol, tetrahydrocannabivarin, cannabidivarin, and cannabichromene, wherein the sorbent comprises an organic and non-hazardous material selected from the group consisting essentially of cellulose, protein-based polymers, hydrocolloid polymers, polypeptide polymers, lipid polymers, or other edible polymers and composites thereof in the form of a permeable and porous matrix or an inorganic and non-hazardous material selected from the group consisting essentially of silica, silica gel, and mixtures thereof, and wherein the vapor, aerosol, or suspension is an aerosol or suspension, and wherein the input comprises one or more nozzles to provide a liquid solvent stream.

13. The system of claim 12, wherein the one or more nozzles are at an end of one or more needles, wherein the edible sorbent is at least partially enclosed in a container, the container being supported in the one or more fluid pathways, wherein the one or more needles are in fluid communication with the interior of the container, and wherein the substance is in a sorbent receptacle in fluid communication with the one or more needles, the one or more fluid pathways, and the output.

14. The system of claim 12, wherein the solvent is forced through the one or more fluid pathways when a user displaces the plunger towards the nozzles.

15. The system of claim 12, wherein the plunger comprises a hollow interior formed by a body member of the plunger and a lid member engaging the body member, wherein the solvent is one or more of coconut oil, olive oil, and canola oil and further comprising a receptacle for the solvent.

16. A apparatus, comprising:
a mesh supporting a herbal substance comprising a substance or component to be ingested that, when heated, forms a vapor, aerosol, or suspension comprising the substance or component to be ingested, the substance or component to be ingested being one or more of tobacco and *cannabis;*
a substrate, positioned downstream at a distance from the mesh, comprising one or more fluid pathways for the vapor, aerosol, or suspension, wherein the vapor, aerosol, or suspension flows through the substrate in a first direction;
an edible sorbent positioned in the one or more fluid pathways to contact the vapor, aerosol, or suspension passing through the one or more fluid pathways to collect a portion of the substance or component to be ingested on the edible sorbent, the component being one or more of nicotine and a cannabinoid, the edible sorbent being permeable or semi-permeable to pass the vapor, aerosol, or suspension;
an output for the vapor, aerosol, or suspension discharged from the one or more fluid pathways after contact with the edible sorbent, the output being in communication with a bag or inhalation device enabling inhalation of the vapor, aerosol, or suspension by a user;
one or more nozzles in fluid communication with the one or more fluid pathways; and
a plunger, in fluid communication with the one or more nozzles, configured to force a liquid solvent through the one or more nozzles while the edible solvent is positioned in the one or more fluid pathways to inject the solvent along the one or more fluid pathways in a second direction to contact the edible sorbent comprising the collected portion of the substance or component to be ingested to provide a food product, wherein the first and second directions are transverse to each other; and wherein:
the liquid solvent is forced through the one or more fluid pathways when a user displaces the plunger towards the nozzles,
the plunger comprises a hollow interior formed by a body member of the plunger and a lid member engaging the body member.

17. The apparatus of claim 16, wherein the vapor, aerosol, or suspension is a vapor, wherein the substance or component to be ingested is one or more of nicotine, tetrahydrocannabinol, cannabinol, cannabigerol, tetrahydrocannabivarin, cannabidivarin, and cannabichromene, wherein the sorbent comprises an organic and non-hazardous material selected from the group consisting essentially of cellulose, protein-based polymers, hydrocolloid polymers, polypeptide polymers, lipid polymers, or other edible polymers and composites thereof in the form of a permeable and porous matrix or an inorganic and non-hazardous material selected from the group consisting essentially of silica, silica gel, and mixtures thereof, and further comprising a heat source, the heat source being positioned near the mesh to heat the herbal substance.

18. The apparatus of claim 17, wherein the mesh is a screen positioned between the heat source and the output, and wherein the output comprises a mouthpiece for a user that enables the user to ingest the discharged vapor, aerosol, or suspension.

19. The apparatus of claim 16 wherein the vapor, aerosol, or suspension is an aerosol or suspension, wherein the sorbent comprises an organic and non-hazardous material selected from the group consisting essentially of cellulose, protein-based polymers, hydrocolloid polymers, polypeptide polymers, lipid polymers, or other edible polymers and composites thereof in the form of a permeable and porous matrix or an inorganic and non-hazardous material selected from the group consisting essentially of silica, silica gel, and mixtures thereof, and wherein the solvent is one or more of coconut oil, olive oil, and canola oil and further comprising a receptacle for the solvent.

20. The apparatus of claim 19, wherein the one or more nozzles are at an end of one or more needles, wherein the edible sorbent is at least partially enclosed in a container, the container being supported in the one or more fluid pathways, wherein the one or more needles are in fluid communication with the interior of the container, and wherein the substance is in a sorbent receptacle in fluid communication with the one or more needles, the one or more fluid pathways, and the output.

* * * * *